(12) United States Patent
Wang et al.

(10) Patent No.: US 7,618,696 B2
(45) Date of Patent: *Nov. 17, 2009

(54) BLOCK COPOLYMER ELASTOMER CATHETER BALLOONS

(75) Inventors: Lixiao Wang, Long Lake, MN (US); Jianhua Chen, Plymouth, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 2088 days.

This patent is subject to a terminal disclaimer.

(21) Appl. No.: 10/080,781

(22) Filed: Feb. 22, 2002

(65) Prior Publication Data

US 2002/0132072 A1    Sep. 19, 2002

Related U.S. Application Data

(60) Continuation of application No. 09/328,781, filed on Jun. 9, 1999, now Pat. No. 6,406,457, which is a continuation of application No. 09/137,658, filed on Aug. 21, 1998, now Pat. No. 5,951,941, which is a division of application No. 08/805,899, filed on Feb. 25, 1997, now Pat. No. 5,830,182, which is a continuation of application No. 08/671,861, filed on Jun. 28, 1996, now abandoned, which is a continuation of application No. 08/397,837, filed on Mar. 2, 1995, now Pat. No. 5,556,383, which is a continuation-in-part of application No. 08/204,554, filed on Mar. 2, 1994, now abandoned.

(51) Int. Cl.
  *B29D 22/00*   (2006.01)
  *B29D 23/00*   (2006.01)
  *B32B 1/08*    (2006.01)

(52) U.S. Cl. .................. 428/36.92; 428/36.9; 428/35.7; 428/220; 428/36.91; 604/264

(58) Field of Classification Search .................. 604/96, 604/264, 280; 606/194; 428/35.7, 36.9, 428/36.92, 36.91, 220
See application file for complete search history.

(56) References Cited

U.S. PATENT DOCUMENTS 4,154,244 A    5/1979    Becker et al. ........... 128/349 B (Continued)

FOREIGN PATENT DOCUMENTS

EP    0 485 903    5/1982

(Continued)

OTHER PUBLICATIONS

Patentee's Response to Opposer's Communication dated Dec. 6, 2004 in the opposition proceeding for EP 748232.

(Continued)

*Primary Examiner*—Michael C Miggins
(74) *Attorney, Agent, or Firm*—Vidas, Arrett & Steinkraus (57) ABSTRACT

Balloons for medical devices, particularly balloon angioplasty catheters, are made from particular block copolymer thermoplastic elastomers in which the block copolymer is made up of hard segments of a polyester or polyamide and soft segments of polyether; the polyester hard segments are polyesters of an aromatic dicarboxylic acid and a $C_2$-$C_4$ diol; the polyamide hard segments are polyamides of $C_6$ or higher carboxylic acids and $C_6$ or higher organic diamines or of $C_6$ or higher aliphatic ω-amino-α-acids, and the polyether soft segments are polyethers of $C_2$-$C_{10}$, diols; the block copolymer has a low flexural modulus, namely less than 150,000 psi; the block copolymer has a hardness, Shore D scale, of greater than 60; and the percentage by weight of the block polymer attributable to the hard segments is between about 50% and about 95%. The polymers provide high strength, thin wall, compliant and semi-compliant balloons, which leads to a low profile catheter. The low profile catheters have very good initial crossing, good trackability, good recrossing after first inflation.

22 Claims, 2 Drawing Sheets

U.S. PATENT DOCUMENTS

| | | | |
|---|---|---|---|
| 4,254,774 A | 3/1981 | Boretos | |
| 4,331,786 A | 5/1982 | Foy et al. | |
| 4,332,920 A | 6/1982 | Foy et al. | |
| 4,385,635 A | 5/1983 | Ruiz | |
| 4,413,989 A | 11/1983 | Schjeldahl et al. | 604/96 |
| 4,456,000 A | 6/1984 | Schjeldahl et al. | 128/1 |
| 4,490,421 A | 12/1984 | Levy | 428/35 |
| 4,563,181 A | 1/1986 | Wijaymathna | |
| 4,675,361 A | 6/1987 | Ward, Jr. | 525/92 |
| 4,786,556 A | 11/1988 | Hu et al. | 428/412 |
| RE32,983 E | 7/1989 | Levy | 604/96 |
| 4,886,506 A | 12/1989 | Lovgren et al. | |
| 4,898,591 A | 2/1990 | Jang et al. | |
| 4,906,244 A | 3/1990 | Pinchuk et al. | |
| 4,917,667 A | 4/1990 | Jackson | |
| 4,938,676 A | 7/1990 | Jackowski et al. | |
| 4,950,239 A | 8/1990 | Gahara et al. | |
| 4,950,257 A | 8/1990 | Hibbs et al. | |
| 4,952,357 A | 8/1990 | Enteneuer | 264/129 |
| 4,963,313 A | 10/1990 | Noddin et al. | 264/563 |
| RE33,561 E | 3/1991 | Levy | 604/96 |
| 5,087,394 A | 2/1992 | Keith | 204/22 |
| 5,108,415 A | 4/1992 | Pinchuk et al. | |
| 5,156,612 A | 10/1992 | Pinchuk et al. | |
| 5,195,969 A | 3/1993 | Wang et al. | 604/96 |
| 5,207,700 A * | 5/1993 | Euteneuer | 606/194 |
| 5,236,659 A | 8/1993 | Pinchuck et al. | |
| 5,250,069 A | 10/1993 | Nobuyoshi et al. | |
| 5,254,091 A | 10/1993 | Aliahmad et al. | 604/96 |
| 5,264,260 A | 11/1993 | Saab | |
| 5,270,086 A | 12/1993 | Hamlin | 604/96 |
| 5,281,677 A | 1/1994 | Onwunaka et al. | 525/458 |
| 5,290,306 A | 3/1994 | Trotta et al. | |
| 5,295,978 A | 3/1994 | Fan et al. | 604/265 |
| 5,300,048 A | 4/1994 | Drewes, Jr. et al. | 604/280 |
| 5,304,134 A | 4/1994 | Kraus et al. | 604/96 |
| 5,304,340 A | 4/1994 | Downey | |
| 5,316,016 A | 5/1994 | Adams et al. | 128/774 |
| 5,328,468 A | 7/1994 | Kaneko et al. | 604/96 |
| 5,334,146 A | 8/1994 | Ozasa | 604/96 |
| 5,335,675 A | 8/1994 | Wheeler et al. | 128/842 |
| 5,342,386 A | 8/1994 | Trotta | 606/194 |
| 5,344,400 A | 9/1994 | Kaneko et al. | 604/96 |
| 5,348,538 A | 9/1994 | Wang et al. | 604/96 |
| 5,358,486 A | 10/1994 | Saab | |
| 5,397,306 A | 3/1995 | Nobuyoshi et al. | 604/96 |
| 5,403,340 A | 4/1995 | Wang et al. | 606/194 |
| 5,411,477 A | 5/1995 | Saab | 604/96 |
| 5,478,320 A | 12/1995 | Trotta | 604/96 |
| 5,500,180 A | 3/1996 | Anderson et al. | 264/532 |
| 5,500,181 A | 3/1996 | Wang et al. | 264/532 |
| 5,512,051 A | 4/1996 | Wang et al. | 604/96 |
| 5,554,120 A | 9/1996 | Chen et al. | 604/96 |
| 5,556,383 A | 9/1996 | Wang et al. | |
| 5,565,523 A | 10/1996 | Chen et al. | 525/176 |
| 5,769,817 A | 6/1998 | Burgmeier | 604/96 |
| 5,807,520 A | 9/1998 | Wang | 264/520 |
| 5,830,182 A | 11/1998 | Wang et al. | |
| 5,951,941 A | 9/1999 | Wang et al. | |
| 6,146,356 A | 11/2000 | Wang et al. | |
| 6,171,278 B1 | 1/2001 | Wang et al. | |
| 6,210,364 B1 | 4/2001 | Anderson et al. | |

FOREIGN PATENT DOCUMENTS

| | | |
|---|---|---|
| EP | 0213750 | 3/1987 |
| EP | 0213752 | 3/1987 |
| EP | 0 349 640 B1 | 2/1988 |
| EP | 274 411 | 7/1988 |
| EP | 0 318 919 | 6/1989 |
| EP | 381919 | 6/1989 |
| EP | 420 488 | 3/1991 |
| EP | 0 436 501 | 7/1991 |
| EP | 0 537 069 A1 | 10/1992 |
| EP | 0 513 459 A1 | 11/1992 |
| EP | 540 858 | 5/1993 |
| EP | 420 488 B | 7/1993 |
| EP | 0 566 755 A1 | 10/1993 |
| EP | 531 117 B1 | 10/1993 |
| EP | 566 755 A | 10/1993 |
| EP | 540 858 A | 12/1993 |
| EP | 592 885 A | 4/1994 |
| EP | 592870 | 4/1994 |
| EP | 606165 | 7/1994 |
| FR | 2 651 681 | 3/1991 |
| JP | 3-176068 | 7/1991 |
| JP | 4-144572 | 5/1992 |
| WO | 84/01513 | 4/1984 |
| WO | WO 89/08473 | 9/1989 |
| WO | 92/08512 | 5/1992 |
| WO | WO 92/08512 | 5/1992 |
| WO | 92/19316 | 11/1992 |
| WO | WO 92/19440 | 11/1992 |
| WO | 95/09667 | 4/1995 |
| WO | WO 95/22367 | 8/1995 |
| WO | 95/23619 | 9/1995 |
| WO | WO 96/04951 | 2/1996 |
| WO | WO 96/12516 | 5/1996 |
| WO | 96/37240 | 11/1996 |

OTHER PUBLICATIONS

Flesher, Jr., "Polyether Block Amide: High-Performance TPE," *Modern Plastics*, pp. 100, 105, 106, 110, (Sep. 1987).

M. Xie, et al, "Etude Morphologique De *Bloc*-Copoly(Ether-Amide)s," *Makromol. Chem.* 187, 383-400 (1986).

H. Boubil, et al, "Morphology of Polyamide and Polyether Block Amide Blends," *Polymer Engineering and Science*, 29, 679-684 (1989).

N. Alberola, et al, "Mechanical Relaxation Processes in Polyether Block Amide Copolymers (PEBA)," *Makromol. Chem., Makromol. Symp.* 23, 219-224 (1989).

H. Faruque, et al, "Study of Multiple Relaxations in Pebax, Polyether Block Amide (PA12 2135 Block PTMG 2032). Copolymer Using the Thermally Stimulated Current Method," *Polymer*, 27, 527-531 (1986).

H. Faruque, et al, "Study of Multiple Relaxations in Pebax, Polyether Block Amide (PA12 2135 Block PTMG 2032), Copolymer Using the Thermally Stimulated Current Method," *Polymer*, 27, 527-531 (1986).CD G. Gordon, "Glass Transition in Nylons," *J. Polymer Sci.: Part A-2*, 9, 1693-1702 (1971).

D. Prevorsek, et al, "Mechanical Relaxations in Polyamides," *J. Polymer Sci.: Part A-2*, 9, 867-886 (1971).

H. Faruque, et al, "A Thermally Stimulated Current Technique for Measuring the Molecular Parameters of Pebax, A Polyether-Block Amide Copolymer," *J. Mater. Sci.*, 22, 675-678 (1987).

R. Koch, "Pebax," *Advances in Polymer Technology*, 2, 160-162 (1982).

N. Alberola, "Micromechanical Properties of Polyether Block Amide Copolymers," *J. Applied Sci.*, 36, 737-804 (1988).

J. Brandrup, et al, eds., Polymer Handbook, John Wiley & Sons (1989), pp. VI/209, VI/243-VI/244.

De, et al, eds. *Thermoplastic Elastomer from Rubber-Plastic Blends*, Chapter 1, Ellis Horwoal, New York pp. 13-27.

Gorski, "The Nomenclature of Thermoplastic Elastomers," Kunstoffe German Plastics, 83 (1993) No. 3, pp. 29-30.

Hofmann, "Thermoplastic Elastomers," Kunstoffe German Plastics, 80 (1990) No. 10, pp. 88-90.

Atochem, "Pebax® Resins 33 Series Property Comparison" undated, (1 pg manufacturers technical information sheet received Sep. 29, 1994).

Atochem, undated and untitled brochure for Pebax® resins, pp. 2-5.

Bhowmick, et al eds., *Handbook of Elastomers*, Chapters 10 and 12, Marcel Dekker Inc., pp. 341-373 and 411-442.

Walker, et al, eds. *Handbook of Thermoplastic Elastomers*, Chapter 8, Van Nostrand Reinhold Co., NY pp. 258-281.
DuPont, "Hytrel®" 11 pg undated product brochure (received Sep. 1990).
Tecoflex® Medical Grade Aliphatic Thermoplastic Polyurethanes, date unknown.
Scimed Leap Trio PTCA Catheters, May 16, 1995.
Dow Processing Guide, Pellethane, date unknown.
Dupont product literature on HYTREL, date unknown.
Dow Chemical product literature on ISOPLAST, Dec. 17, 1991 and other dates unknown.
Tecothane® Medical Grade Aliphatic Thermoplastic Polyurethanes, date unknown.
Thermopolastic Elastomer data sheet, D.A.T.A. Business Publishing, p. 2-1709 1994.
Polyamide-Nylon data sheet, D.A.T.A. Business Publishing, p. 2-595 1994.
International Serach Report, International Application PCT/US 95/02717.
Polyether Block Amide data sheet, D.A.T.A. Business Publishing, p. 2-837 1994.
Tecoplast™ Engineering Polyurethane Resins May 1996.

"Thermoplastic Elastomer," Kagaku Kogyo Nipposha, published Feb. 15, 1992, pp. 23-39 and 225-229 with partial translation.
*Ullmann's Encyclopedia of Industrial Chemistry* (1995), vol. A26, Cpt 4, "Thermoplastic Elastomers," pp. 651-655.
"ISO 178, Plastics—Determination of flexural properties," ISO, 2001.
"ASTM D 790-03 Standard Test Methods for Flexural Properties of Unreinforced and Reinforced Plastics and Electric Materials," ASTM, 2003.
Opponents letter of Mar. 24, 2006 in Opposition proceeding against EP 0748232.
Patentee's reply of Apr. 20, 2006 in Opposition proceeding against EP 0748232.
Minutes of Apr. 26, 2006 in Oral Proceedings in Opposition proceeding against EP 0748232.
An interlocutory decision issued by the Opposition Division of the European Patent Office dated Jun. 28, 2002 in connection with EP 748232.
The opponent's grounds for appeal dated Oct. 15, 2002.
The patentees counterstatement to the appeal dated May 5, 2003.
The Opponents reply to the counterstatement dated Nov. 15, 2004.
Documents D1-D40 cited in the opposition.

* cited by examiner

BLOCK COPOLYMER ELASTOMER CATHETER BALLOONS

CROSS REFERENCE TO RELATED APPLICATIONS

This application is a continuation of U.S. application No. 09/328,781, filed Jun. 9, 1999, now U.S. Pat. No. 6,406,457 allowed; which is a continuation of U.S. application No. 09/137,658, filed Aug. 21, 1998, now U.S. Pat. No. 5,951,941; which is a division of U.S. application No. 08/805,899, filed Feb. 25, 1997, now U.S. Pat. No. 5,830,182; which is a continuation of U.S. application No. 08/671,861, filed Jun. 28, 1996, now abandoned; which is a continuation of U.S. application No. 08/397,837, filed Mar. 2, 1995, now U.S. Pat. No. 5,556,383; which is a continuation-in-part of U.S. application No. 08/204,554, filed Mar. 2, 1994, now abandoned. The patents listed above are all incorporated herein by reference in their entirety.

BACKGROUND OF THE INVENTION

Balloons mounted on the distal ends of catheters are widely used in medical treatment. The balloon may be used widen a vessel into which the catheter is inserted or to force open a blocked vessel. The requirements for strength and size of the balloons vary widely depending on the balloon's intended use and the vessel size into which the catheter is inserted. Perhaps the most demanding applications for such balloons are in balloon angioplasty in which catheters are inserted for long distances into extremely small vessels and used to open stenoses of blood vessels by balloon inflation. These applications require extremely thin walled high strength relatively inelastic balloons of predictable inflation properties. Thin walls are necessary because the balloon's wall and waist thicknesses limit the minimum diameter of the distal end of the catheter and therefore determine the limits on vessel size treatable by the method and the ease of passage of the catheter through the vascular system. High strength is necessary because the balloon is used to push open a stenosis and so the thin wall must not burst under the high internal pressures necessary to accomplish this task. The balloon must have some elasticity so that the inflated diameter can be controlled, so as to allow the surgeon to vary the balloon's diameter as required to treat individual lesions, but that elasticity must be relatively low so that the diameter is easily controllable. Small variations in pressure must not cause wide variation in diameter.

While angioplasty balloons are considered inelastic relative to balloons used in most other applications, there is in the art a general classification of such balloons based on their expandability or "compliance" relative to each other. As used herein, "non-compliant" balloons are the least elastic, increasing in diameter about 2-7%, typically about 5%, as the balloon is pressurized from a inflation pressure of about 6 atm to a pressure of about 12 atm, that is, they have a "distension" over that pressure range of about 5%. "Semi-compliant" balloons have somewhat greater distensions, generally 7-16% and typically 10-12% over the same pressurization range. "Compliant" balloons are still more distensible, having distensions generally in the range of 16-40% and typically about 21% over the same pressure range. Maximum distensions, i.e. distension from nominal diameter to burst, of various balloon materials may be significantly higher than the distension percentages discussed above because wall strengths, and thus burst pressures, vary widely between balloon materials. The 6-12 atm inflation range is used in the present application to allow direct comparison of the compliance attributes of various balloons.

The strength of the polymer materials used in the balloons varies widely. The strongest balloons are also the most inelastic, being made of highly orientable polymers such as polypropylene, polyethylene terephthalate or other phthalate polyesters or copolyesters, and nylons. Tensile wall strengths are commonly 20,000-50,000 psi. Commercial angioplasty balloons made of such materials with nominal diameters in the range of 1.5-4.5 mm have distensions in the non-compliant to semi-compliant range and can often be rated to pressures of 16 atm or higher without risk of bursting (actual burst pressures may exceed 20 atm). Generally, however, as compliance increases the wall strength decreases. Other semi-compliant and compliant balloons are made of less highly orientable polymers such as ethylene-vinyl acetate, polyvinyl chloride, olefin copolymers and ionomer resins. The wall strengths of balloons made from these less orientable materials are still lower than those made from the highly orientable polymers, commonly in the range of 6,000-15,000 psi, resulting in lower rated maximum inflation pressures of 9-10 atm.

The particular distension and maximum pressure attributes of a balloon are also influenced both by polymer type and by the conditions under which the balloon is blown. Angioplasty balloons are conventionally made by blowing a tube of polymer material at a temperature above its glass transition temperature. For any given balloon material, there will be a range of distensions achievable depending on the conditions chosen for the blowing of the balloon.

In U.S. Pat. No. 4,906,244 to Pinchuck there are described balloons of nylon (i.e. aliphatic polyamide) materials, such as nylon 12, nylon 11, nylon 9, nylon 6/9 and nylon 6/6. Like all other polymer materials the distensions of these balloons can be determined, within a range, by controlling blowing conditions such as initial dimensions of tubing, prestretching, hoop ratio and heat set conditions. The data in the reference show that compliance characteristics can be obtained ranging from non-compliant to semi-compliant characteristics and that wall strengths of greater than 15,000 can be obtained. The reference suggests that higher compliances can be achieved with nylon materials but there is no indication of what other nylons or other balloon forming conditions could be employed to do so.

It has also been suggested to prepare balloons of thermoplastic elastomers in U.S. Pat. No. 4,254,774 to Boretos, and polyamide elastomers have been mentioned among a number of possible balloon materials suggested in U.S. Pat. No. 5,250,069 to Nobuyoshi, et al, but there are many of such thermoplastic elastomer polymers and before the invention hereof it has been expected that performance of balloons made from these materials would not be generally any better than high to intermediate compliance made from conventional thermoplastic polymers such as polyethylene ionomer, polyvinyl chloride, polyethylene or ethylene-vinyl acetate.

In U.S. Pat. No. 5,290,306 polyester ethers and polyetheresteramide polymers of Shore D hardness less than 55 have been proposed for use as a sleeve or co-extruded outer layer to a balloon of a biaxially oriented nylon or polyethylene terephthalate (PET) material, so as to provide the balloon with improved softness and pin-hole and abrasion resistance.

Polyurethane block copolymers having flexural modulus of about 190,000 and an ultimate elongation of 250% are disclosed as balloon materials in EP 0592885 and mention is made of also using polyester block copolymers or polyamide block copolymers but no suggestion is made that such alternative copolymers could be usefully employed if their flexural modulus was substantially lower or their ultimate elongation was substantially higher than the disclosed polyurethane block copolymers.

SUMMARY OF THE INVENTION

New balloon materials, which possess a unique combination of physical properties including non-compliant, semi-compliant and compliant distension attributes, good flexibility and high tensile strength, are made from particular block copolymer thermoplastic elastomers characterized as follows:

the block copolymer is made up of hard segments of a polyester or polyamide and soft segments of polyether; the polyester hard segments are polyesters of an aromatic dicarboxylic acid and a $C_2$-$C_4$ diol, the polyamide hard segments are polyamides of $C_6$ or higher, preferably $C_{10}$-$C_{12}$, carboxylic acids and $C_6$ or higher, preferably $C_{10}$-$C_{12}$, organic diamines or of $C_6$ or higher, preferably $C_{10}$-$C_{12}$, aliphatic $\zeta$-amino-$\alpha$-acids, and the polyether soft segments are polyethers of $C_2$-$C_{10}$, preferably $C_4$-$C_6$ diols;

the block copolymer has a low flexural modulus, namely less than 150,000 psi, preferably less than 120,000 psi; the block copolymer has a hardness, Shore D scale, of greater than 60; and the percentage by weight of the block polymer attributable to the hard segments is between about 50% and about 95%.

From such polymers, balloons having compliant to semi-compliant expansion profiles can be prepared with wall strengths greater than 15,000 psi, frequently greater than 20,000 psi. The high strength of the balloons produced from the polymers allows for construction of low profile catheters and the low flexural modulus contributes to a softer feel found with the balloons of the invention, compared to those made of other high strength polymer materials. Low profile catheters made with the inventive balloons have very good initial crossing, good trackability and good recrossing after first inflation.

DETAILED DESCRIPTION OF THE INVENTION

The preferred balloons of the invention are made of polyamide/polyether block copolymers. The polyamide/polyether block copolymers are commonly identified by the acronym PEBA (polyether block amide). The polyamide and polyether segments of these block copolymers may be linked through amide linkages, however, most preferred are ester linked segmented polymers, i.e. polyamide/polyether polyesters. Such polyamide/polyether/polyester block copolymers are made by a molten state polycondensation reaction of a dicarboxylic polyamide and a polyether diol. The result is a short chain polyester made up of blocks of polyamide and polyether. The polyamide and polyether blocks are not miscible. Thus the materials are characterized by a two phase structure: one is a thermoplastic region that is primarily polyamide and the other is elastomer region that is rich in polyether. The polyamide segments are semicrystalline at room temperature. The generalized chemical formula for these polyester polymers may be represented by the following formula:

in which PA is a polyamide segment, PE is a polyether segment and the repeating number n is between 5 and 10.

The polyamide segments are suitably aliphatic polyamides, such as nylons 12, 11, 9, 6, 6/12, 6/11, 6/9, or 6/6. Most preferably they are nylon 12 segments. The polyamide segments may also be based on aromatic polyamides but in such case significantly lower compliance characteristics are to be expected. The polyamide segments are relatively low molecular weight, generally within the range of 500-8,000, more preferably 2,000-6,000, most preferably about 3,000-5,000.

The polyether segments are aliphatic polyethers having at least 2 and no more than 10 linear saturated aliphatic carbon atoms between ether linkages. More preferably the ether segments have 4-6 carbons between ether linkages, and most preferably they are poly(tetramethylene ether) segments. Examples of other polyethers which may be employed in place of the preferred tetramethylene ether segments include polyethylene glycol, polypropylene glycol, poly(pentamethylene ether) and poly(hexamethylene ether). The hydrocarbon portions of the polyether may be optionally branched. An example is the polyether of 2-ethylhexane diol. Generally such branches will contain no more than two carbon atoms. The molecular weight of the polyether segments is suitably between about 400 and 2,500, preferably between 650 and 1000.

The weight ratio of polyamide to polyether in the polyamide/polyether polyesters used in the invention desirably should be in the range of 50/50 to 95/5, preferably between 60/30 and 92/08, more preferably, between 70/30 and 90/10.

Polyamide/polyether polyesters are sold commercially under the PEBAX trademark by Atochem North America, Inc., Philadelphia Pa. Examples of suitable commercially available polymers are the Pebax® 33 series polymers with hardness 60 and above, Shore D scale, especially Pebax® 7033 and 6333. These polymers are made up of nylon 12 segments and poly(tetramethylene ether) segments in about 90/10 and about 80/20 weight ratios, respectively. The average molecular weight of the individual segments of nylon 12 is in the range of about 3,000-5,000 grams/mole and of the poly(tetramethylene ether) segments are in the ranges of about 750-1,250 for the 6333 polymer and about 500-800 for the 7033 polymer. The inherent viscosities of these polymers are in the range of 1.33 to 1.50 dl/g.

Generally speaking, balloons of Pebax® 7033 type polymer exhibit borderline non-compliant to semi-compliant behavior and balloons of Pebax® 6333 type polymer show semi-compliant to compliant distension behavior, depending on the balloon forming conditions.

While the Pebax®-type polyamide/polyether polyesters are most preferred, it is also possible to use other PEBA polymers with the physical properties specified herein and obtain similar compliance, strength and softness characteristics in the finished balloon.

As an alternative to polyamide elastomers, it is also possible to utilize polyester/polyether segmented block copolymers and obtain similar balloon properties. Such polymers are made up of at least two polyester and at least two polyether segments. The polyether segments are the same as previously described for the polyamide/polyether block copolymers useful in the invention. The polyester segments are polyesters of an aromatic dicarboxylic acid and a two to four carbon diol.

Suitable dicarboxylic acids used to prepare the polyester segments of the polyester/polyether block copolymers are ortho-, meta- or para- phthalic acid, napthalenedicarboxylic acid or meta-terphenyl-4,4'-dicarboxylic acids.

Preferred polyester/polyether block copolymers are poly(butylene terephthalate)-block-poly(tetramethylene oxide) polymers such as Arnitel EM 740, sold by DSM Engineering Plastics. Hytrel polymers, sold by DuPont which meet the physical and chemical specifications set out herein can also be used, but are less preferred.

It is believed important that the block copolymers have a hardness, Shore D scale, of at least 60 and a flexural modulus of no more than about 150,000, in order to obtain the desirable combination of strength, compliance and softness characteristics which distinguish the inventive balloons. Preferably the Shore D hardness is in the range of 65-75 and the flexural modulus is in the range of 50,000-120,000. The preferred polymers useful in the invention are also characterized by a high ultimate elongation of about 300% or higher and an ultimate tensile strength of at least 6,000 psi.

The balloons of the invention are made using known techniques for forming catheter balloons. For coronary angioplasty catheter balloons (balloon diameters of about 1.5-4.0 mm), single wall thicknesses of less than 0.001 inches, preferably less than 0.0007 inches, are readily obtained. Wall strengths for such balloons are in excess of 15,000, typically at least 18,000 psi, and in most cases in the range of about 20,000 to 32,000 psi. For peripheral angioplasty, balloons of up to 10 mm diameter may be used and in such cases somewhat thicker walls may be employed. Even with a 10 mm balloon, wall thicknesses of about 0.0015 mm or less can be employed to provide balloons with burst pressures of at least 10 atm. Suitably the balloons are formed by expansion of tubing at a hoop ratio (mold diameter/tubing ID) of between 3 and 8, preferably between 4 and 7.

The following examples illustrate the preparation and unique properties of balloons of the invention.

EXAMPLES

Tubing Extrusion

In examples 1-9, 11 and 13, all tubing materials were made from Atochem Pebax® 7033 and Pebax® 6333 by extrusion. Polymer pellets were dried to less than 0.10 wt % moisture content before extrusion. Tubing was extruded at melt temperature range of 200° C. to 220° C. by hot feedthroat through seven extruder zones with controlled temperatures. The extrusion conditions were based upon manufacturer's recommended polymer processing conditions. After the polymer material extruded out of the die in tube form it passed through a small air gap and was cooled in a deionized water bath maintained at about 65° F. A puller was used to pull the tube through the water bath. After passing through the puller, the extruded tubing was cut into 8 inch sections or spooled. A variety of tubing sizes were made by this method.

Example 1

The product of this example is a 2.25 mm balloon made from Pebax® 7033. This polymer has a Shore D hardness of 69, a flexural modulus of 67,000, an ultimate tensile strength of 8,300 psi and an ultimate elongation of 400%. The tubing sections had an OD of 0.0270 inch and an ID of 0.0179 inch. In order to form a 2.25 mm balloon with a 20 mm body length, a mold having dimensions that allowed the tube to blow out to the appropriate body size and balloon waist inner diameters was used.

After the tubing section was securely inside the mold, the mold was placed in a holder. The tubing section extended out the top of the mold and was fed into a Touhy clamp through which nitrogen gas applied to the inner lumen of the tubing at 280 psi with tension applied to the tubing. The tubing section at the bottom of the mold was clamped off such that the pressure was maintained inside the tubing section. The mold was then gradually dipped into a deionized hot water bath maintained at 90° C. (±1° C.) to a point just above the proximal waist portion of the mold at a controlled manner. A balloon was formed by radial expansion with internal pressure using a hoop ratio of 5.1. After the balloon formed, the mold was removed from the hot water bath and cooled for approximately 10 sec in a deionized water bath maintained at about 10° C.

Balloons prepared in this manner were subjected to standard burst tests by measuring the double wall thickness of the deflated balloon, inflating the balloon at incrementally increasing pressures and measuring the outside diameter at each increment until the balloon burst. Burst strength, distension and balloon wall strength were calculated from the data obtained. Average results are given in Table 1.

Example 2

The product of this example is a 3.00 mm balloon made from Pebax® 7033. The tubing sections had an OD of 0.0290 inch and an ID of 0.0179 inch. A 3.00 mm size mold was used to produce the balloons. These 3.00 mm balloons were made by the same procedure used in example 1, except for the water bath temperature and internal blowing pressure. The water bath temperature and the pressure were maintained at 95° C. and 300 psi, respectively. The hoop ratio of the balloon was 6.2. The results of testing for burst, distension and wall strength are also listed in Table 1.

Example 3

The product of this example is a 3.00 mm balloon made from Pebax® 7033. The tubing sections had an OD of 0.0316 inch and an ID of 0.0179 inch. A corresponding size mold was used to mold balloons. In this example, 90° C. water bath and 400 psi internal blowing pressure were used. The test results provided in Table 1 show that these balloons gave a higher burst pressure than the previous examples.

Example 4

The product of this example is a 3.00 mm balloon made from Pebax® 7033. The tubing sections had an OD of 0.0320 inch and an ID of 0.0215 inch. A 3.00 mm size mold was used to produce the balloons. The same molding conditions described in example 2 were used except that the tubing was prestretched at room temperature before molding balloons. The prestretch stretching ratio λ was 1.5 in this example. The test results of this example are listed in Table 1.

TABLE 1

Burst and Distension Test Results of Pebax ® 7033 Material (averages of at least 5 balloons).

| Example | Balloon Size (mm) | Single Wall Thickness (inch) | Burst Pressure (psi) | Distension 88 psi-Burst (%) | Distension 88 psi-132 psi (%) | Distension 88 psi-176 psi (%) | Wall Strength psi |
|---|---|---|---|---|---|---|---|
| 1 | 2.25 | 0.00042 | 230 | 21.3 | 4.2 | 10.9 | 25400 |
| 2 | 3.00 | 0.00047 | 230 | 12.7 | 3.2 | 7.1 | 29200 |
| 3 | 3.00 | 0.00060 | 260 | 12.8 | 3.6 | 6.9 | 25900 |
| 4 | 3.00 | 0.00049 | 220 | 23.5 | 4.4 | 9.0 | 26300 |

Example 5

Figure 1:
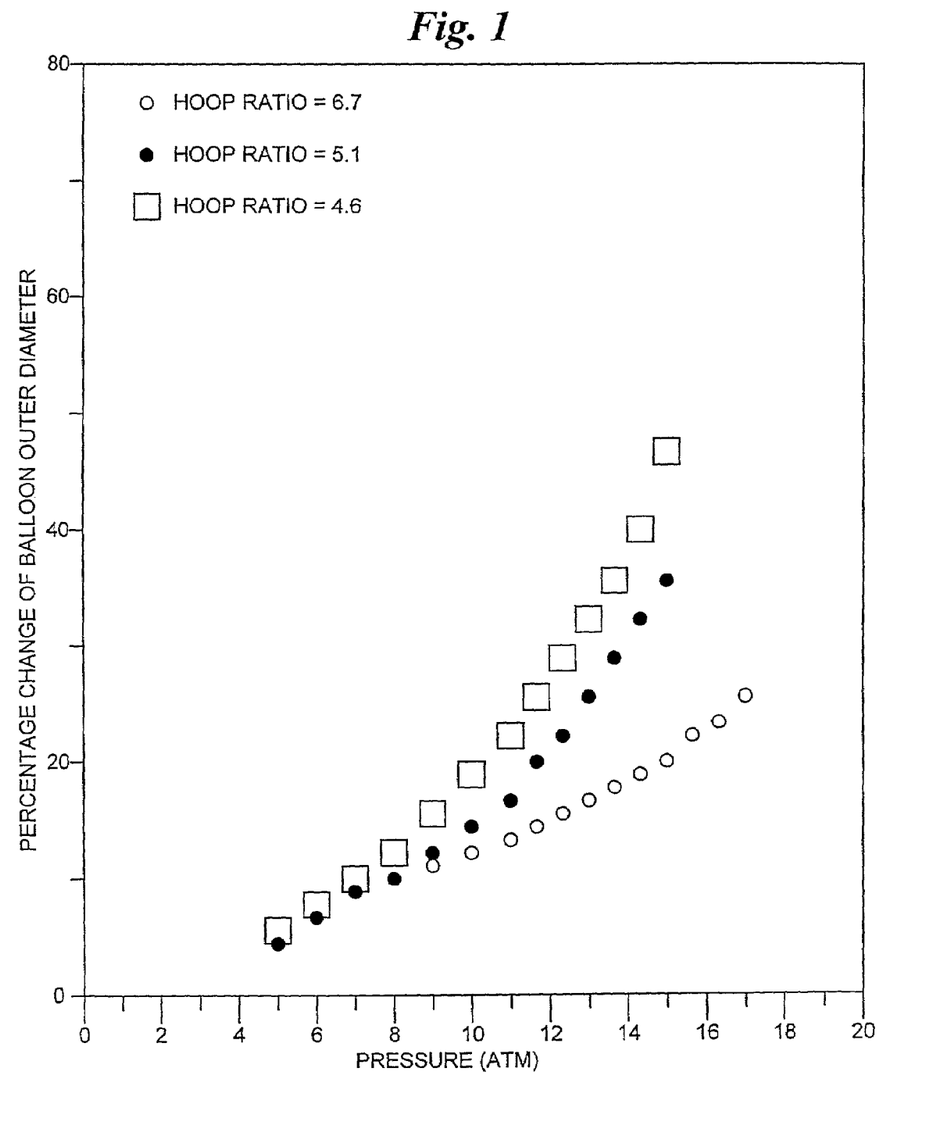
FIG. 1 is a graph of the distension from nominal diameter to burst of several balloons of the invention prepared from a polyamide/polyether polyester block copolymer using different hoop ratios to form the balloon.

Balloons having 2.0-3.0 mm diameters were prepared from Pebax® 7033 using hoop ratios of 4.6, 5.1 and 6.7. The balloons were expanded incrementally at 37° C. until they burst. The results, plotted in FIG. 1, show semi-compliant curves with very high burst strengths ranging from 15-18 atm and maximum distensions at burst of 24%-45%.

Example 6

In this example, balloons were made from Pebax® 6333. This polymer has a Shore D hardness of 63, a flexural modulus of 49,000, an ultimate tensile strength of 8,100 psi and an ultimate elongation of 300%. The same balloon forming procedure as in example 1 was used, except as noted below. The product of this example is a 2.5 mm balloon. The tubing sections had an OD of 0.0316 inch and an ID of 0.0179 inch. A 2.5 mm size mold was used to produce the balloons. In this example, a 95 ° C. water bath and a 300 psi internal blowing pressure were used. The hoop ratio for blowing the balloon was 5.5. The results of burst, distension and wall strength are shown in Table 2.

Example 7

Pebax® 6333 tubing with an OD of 0.0310 inch and an ID of 0.0170 inch was used to produce 3.0 mm balloon. The water bath temperature was 90° C. and the internal blow pressure was 300 psi. The hoop ratio for blowing the balloon was 6.9. Test results are shown in Table 2.

TABLE 2

Burst and Distension Test Results of Pebax ® 6333 Material (averages of at least five balloons)

| Example | Balloon Size (mm) | Single Wall Thickness (inch) | Burst Pressure (psi) | Distension 88 psi-Burst (%) | Distension 88 psi-132 psi (%) | Distension 88 psi-176 psi (%) | Wall Strength (psi) |
|---|---|---|---|---|---|---|---|
| 6 | 2.50 | 0.00058 | 220 | 33.7 | 3.4 | 17.4 | 19900 |
| 7 | 3.00 | 0.00049 | 210 | 17.1 | 4.2 | 9.7 | 26100 |

Example 8

Figure 2:
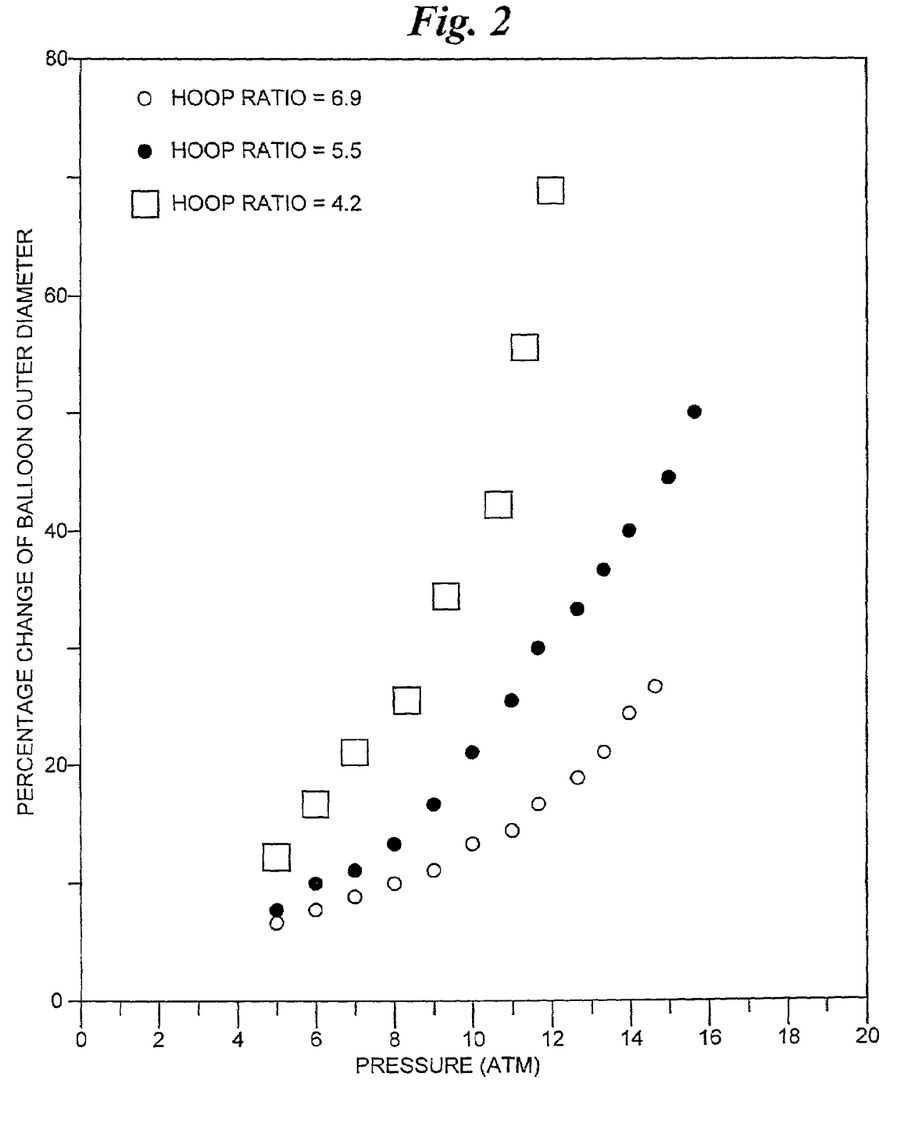
FIG. 2 is a graph as in FIG. 1 using an alternate polyamide/polyether polyester block copolymer to form the balloon of the invention.

Balloons having 2.25-3.0 mm diameters were prepared from Pebax® 6333 using hoop ratios of 4.2, 5.5 and 6.9. The balloons were expanded incrementally at 37° C. until they burst. The results, plotted in FIG. 2, show semi-compliant and compliant curves with burst strengths of 11.5-14 atm and distensions at burst of 23%-69%.

Example 9

The products of this example were 3.00 mm balloons made from Pebax® 6333. The tubing sections had an OD of 0.0350 inch and an ID of 0.0190 inch. A 3.00 mm size mold was used to produce the balloons. Portions of the tubing sections were prestretched at a stretching ratio of 2 ($\lambda=2$) before molding the balloons. The prestretched portions were on either side of a central 8 mm unstretched portion protected during the prestretching operation by a clamp. The unstretched central portion was then formed into a 20 mm long, 3.0 mm diameter balloon body by expansion under pressure in a mold as in the previous examples. The temperature of the water bath was 95° C. and the expansion pressure was 340 psi. The balloons made in this manner had a hoop ratio of 6.2, a single body wall thickness of between 0.0006 and 0.0007 inches, a distal waist wall thickness of between 0.0014 and 0.0021 inches a proximal waist wall thickness of between 0.0014 and 0.0018 inches. The burst pressure of the balloons was about 270 psi. The balloon distension was semi-compliant.

Example 10

The material used in this example was Arnitel EM 740 sold by DSM Engineering Plastics. This polymer had a Shore hardness of 74D, a flexural modulus 120,000 psi , an ultimate tensile strength of 6,400 psi and an ultimate elongation of 340%. 2.25 mm Balloons were prepared from tubing of dimensions OD=0.0270 inches and ID=0.0179 inches. The tubing was necked at two ends and the balloon body portion was unstretched, as described in Example 9. The molding temperature was 80° C. The molding pressure was 290 psi. The molding tension was 50 grams. Balloon properties are given in Table 3.

TABLE 3

Burst and Distention Test Results of Arnitel EM 740 Material

| Example | Balloon Size (mm) | Single Wall Thickness (inch) | Burst Pressure (psi) | Distention 88-Burst % | Distention 88-132 % | Distention 88-176 % | Wall Strength (psi) |
|---|---|---|---|---|---|---|---|
| 11 | 2.25 | 0.00041 | 238 | 34 | 6.2 | 16.7 | 25,700 |

Example 11

The material used in this example was Pebax 7033. The molding temperature was 95° C. The molding pressure was 500 psi. 2.00 mm Balloons were prepared from tubing segments as set forth below. All tubing segments were stretched at room temperature with different stretching ratios and starting tubing dimensions. The unit of ID and OD is inches.

a: the tubing was stretched at λ=2.5 stretching ratio starting ID=0.0130, OD=0.0252 ending ID=0.0087, OD=0.0177 b: the tubing was stretched a λ=3.0 stretching ratio starting ID=0.0132, OD=0.0252 ending ID=0.0081, OD=0.0162 c: the tubing was stretched at λ=4.5 stretching ratio starting ID=0.0132, OD=0.0262 ending ID=0.0064, OD=0.0136

The properties of the resulting balloons are set forth in Table 4.

TABLE 4

Burst and Distention Test Results of Pebax 7033 Material

| Example | Balloon Size (mm) | Single Wall Thickness (inch) | Burst Pressure (psi) | Distention 88-Burst (%) | Distention 88-132 (%) | Distention 88-176 (%) | Wall Strength (psi) |
|---|---|---|---|---|---|---|---|
| 12a | 2.0 | 0.00058 | 279 | 14.6 | 4.0 | 6.5 | 18,900 |
| 12b | 2.0 | 0.00060 | 279 | 14.6 | 3.5 | 6.6 | 18,300 |
| 12c | 2.0 | 0.00062 | 353 | 22.2 | 3.0 | 5.4 | 22,600 |

Example 12

The material used in this example was Arnitel EM 740 poly(butylene terephthalate-block-poly(tetramethylene oxide). 2.75 mm Balloons were prepared from tubing of dimensions: OD=0.0390 inches and ID=0.0230 inches. The tubing was stretched at room temperature at λ=4.8. The dimension of stretched tube was: OD=0.0250 inches and ID=0.0200 inches. The molding temperature was 80° C. The molding pressure was 490 psi. The molding tension was 30 grams. The properties of the resulting balloons are set forth in Table 5.

Example 13

Pebax 7033 tubes with dimensions 0.0198 inch OD and 0.0339 inch ID is drawn at room temperature with a central region protected by an inserted hypo tube approximately 0.018 inch in diameter and 1.0 inch in length. The tube was drawn until an 8 mm central region remained undrawn. Ten sterilized balloons (3.0 mm in diameter and 20 mm in length) with an average double wall thickness 0.00142 inch are made by radially expanding the 8 mm central tubing portion at 95° C. The resulting burst pressure is 270-280 psi and the distension is 9% over the range 88-176 psi and 16% over the range 88-235 psi.

Comparative Examples

Comparative Examples A-C

The material used in this example was Pebax 3533. This polymer has a Shore D hardness of 35 and a flexural modulus of 2,800. Balloons were made by expanding tubes of ID=0.0330 inch and OD=0.0480 inch. The molding temperature was 66° C. The molding pressure was 80 psi. Distension and burst were run at room temperature (22° C.). Balloon properties are set forth in Table 6.

TABLE 5

Burst and Distention Test Results of Arnitel EM 740 Material

| Example | Balloon Size (mm) | Single Wall Thickness (inch) | Burst Pressure (psi) | Distention 88-Burst % | Distention 88-132 % | Distention 88-176 % | Wall Strength (psi) |
|---|---|---|---|---|---|---|---|
| 13 | 2.75 | 0.00066 | 265 | 43.9 | 8.0 | 18.2 | 21,700 |

TABLE 6

Burst and Distention Test Results of Pebax 3533 Material

| Comparative Example | Balloon Size (mm) | Single Wall Thickness (inch) | Burst Pressure (psi) | Distention 10-Burst % | Wall Strength (psi) |
|---|---|---|---|---|---|
| A | 1.50 | 0.00495 | 75 | 67 | 450 |
| B | 2.00 | 0.00218 | 50 | 89 | 900 |
| C | 2.50 | 0.00185 | 40 | 73 | 1060 |

Comparative Example D

The material used in this example was Pebax 5533. This polymer has a Shore D hardness of 55 and a flexural modulus of 29,000. 3.00 mm balloons were prepared from tubing sections having an ID of 0.0190 inch and an OD of 0.0360 inch. The molding temperature was 87.5° C. The molding pressure was 300 psi. Portions of the tubing sections were prestretched at a stretching ratio of 2 ($\lambda$=2) before molding the balloons. The prestretched portions were on either side of an 8 mm central unstretched portion protected during the prestretching operation by a hypo tube as in example 13. The unstretched central portion was then formed into a 20 mm long, 3.0 mm diameter balloon body by expansion under pressure in a mold. Balloon properties are set forth in Table 7.

TABLE 7

Burst and Distention Test Results of Pebax 5533 Material

| Comparative Example | Balloon Size (mm) | Single Wall Thickness (inch) | Burst Pressure (psi) | Distention 88-burst % | Distention 88-132 | Distention 29.4-Burst % | Wall Strength (psi) |
|---|---|---|---|---|---|---|---|
| D | 3.00 | 0.00073 | 132 | 17.0 | 17.0 | 44.3 | 10,700 |

Comparative Examples E-G

The material used in this example was Riteflex 640 poly(butylene terephthalate-block-poly(tetramethylene oxide). This polymer has a Shore D hardness of 40 and a flexural modulus of 12,300. Balloons were made by expanding tubes of ID =0.0360 inch and OD=0.0430 inch. The molding temperature was 80° C. The molding pressure was 80 psi. Balloon properties are set forth in Table 8.

TABLE 8

Burst and Distention Test Results of Riteflex 640 Material

| Comparative Example | Balloon Size (mm) | Single Wall Thickness (inch) | Burst Pressure (psi) | Distention 10-Burst % | Wall Strength (psi) |
|---|---|---|---|---|---|
| E | 1.50 | 0.00216 | 80 | 66 | 1100 |
| F | 1.75 | 0.00105 | 65 | 52 | 2100 |
| G | 2.25 | 0.00088 | 60 | 62 | 3020 |

What is claimed is:

1. A medical device comprising a balloon, the balloon formed from a block copolymer thermoplastic elastomer polymer, the polymer being characterized by a flexural modulus of 150,000 psi or less and a Shore D hardness of at least 60, the balloon having a single wall thickness of less than 0.001 inches and a wall strength in excess of 15,000 psi.

2. A medical device as in claim 1 wherein the wall strength of the balloon is in excess of 20,000 psi.

3. A medical device as in claim 1 wherein the polymer is further characterized by an ultimate elongation of 300% or higher.

4. A medical device as in claim 1 wherein the balloon has a nominal diameter of 1.5-10 mm.

5. A medical device as in claim 1 further comprising a catheter having a distal end, said balloon being mounted on the catheter near said distal end.

6. A medical device as in claim 1 wherein the block copolymer is further characterized by a ultimate tensile strength of at least 6,000 psi.

7. A medical device as in claim 1 wherein the polymer has a Shore D hardness of at least 63.

8. A medical device as in claim 1 wherein the block copolymer has a Shore D hardness in the range of 65-75 and a flexural modulus in the range of 50,000-120,000 psi.

9. A medical device as in claim 8 wherein the block copolymer is represented by the formula:

in which PA is a polyamide segment of molecular weight in the range of 500-8,000; PE is a polyether segment of molecular weight in the range of 500-2,500 and the repeating number n is between 5 and 10.

10. A medical device as in claim 9 wherein the block copolymer segment, PA, is an aliphatic polyamide of one or more $C_{10}$-$C_{12}$ aliphatic acids and one or more $C_{10}$-$C_{12}$ aliphatic diamines or of a $C_{10}$-$C_{12}$ aliphatic ω-amino-α-acid.

11. A medical device as in claim 9 wherein the polyamide segment, PA, is selected from the group consisting of nylon 12, nylon 11, nylon 9, nylon 6, nylon 6/12, nylon 6/11, nylon 6/9 and nylon 6/6.

12. A medical device as in claim 9 wherein the polyamide segment, PA, is nylon 12 of a molecular weight of 3,000-5,000, and the polyether segment, PE, is poly(tetramethylene ether) of molecular weight between 500 and 1250.

13. A medical device as in claim 9 wherein the polyamide segments, PA, comprise between 80 and 90% by weight of the polyamide/polyether polyester.

14. A medical device as in claim 9 wherein said polyether segment, is selected from the group consisting of poly(tetramethylene ether), poly(pentamethylene ether) and poly(hexamethylene ether).

15. A medical device as in claim 1 wherein the polymer is a polyether-block-amide copolymer comprising at least two polyamide hard segments and at least two polyether soft segments.

16. A medical device as in claim 15 wherein the polyamide hard segments are polyamides of $C_6$ or higher carboxylic acids and $C_6$ or higher organic diamines or of $C_6$ or higher aliphatic ω-amino-α-acids, and the polyether soft segments are polyethers of $C_2$-$C_{10}$ diols.

17. A medical device as in claim 16 wherein the percentage by weight of the block copolymer attributable to the hard segments is between about 50% and about 95%.

18. A medical device as in claim 1 wherein the polymer is a polyester-block-ether copolymer comprising at least two polyester hard segments and at least two polyether soft segments.

19. A medical device as in claim 18 wherein the polyester hard segments are polyesters of an aromatic dicarboxylic acid and a $C_2$-$C_4$ diol and the polyether soft segments are polyethers of $C_2$-$C_{10}$ diols.

20. A medical device as in claim 19 wherein the percentage by weight of the block copolymer attributable to the hard segments is between about 50% and about 95%.

21. A medical device as in claim 18 wherein said polyester segments are polyesters of an acid selected from the group consisting of ortho-, meta- or para- phthalic acid, napthalene-dicarboxylic acid and meta-terphenyl-4,4'-dicarboxylic acids and a diol selected from the group consisting of ethylene glycol, 1,3-propane diol and 1,4-butane diol.

22. A medical device as in claim 18 wherein the block copolymer is poly(butylene terephthalate-block-poly(tetramethylene oxide).

* * * * *